United States Patent
Stocco et al.

(10) Patent No.: US 10,695,574 B2
(45) Date of Patent: Jun. 30, 2020

(54) SENSORY INPUT THROUGH NON-INVASIVE BRAIN STIMULATION

(71) Applicant: University of Washington, Seattle, WA (US)

(72) Inventors: Andrea Stocco, Seattle, WA (US); Darby Losey, Seattle, WA (US); Justin A. Abernethy, Seattle, WA (US); Rajesh Rao, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 457 days.

(21) Appl. No.: 15/299,875

(22) Filed: Oct. 21, 2016

(65) Prior Publication Data
US 2017/0113056 A1    Apr. 27, 2017

Related U.S. Application Data

(60) Provisional application No. 62/244,582, filed on Oct. 21, 2015.

(51) Int. Cl.
*A61N 2/00* (2006.01)
*A61N 2/02* (2006.01)
(Continued)

(52) U.S. Cl.
CPC .......... *A61N 2/006* (2013.01); *A61B 5/4005* (2013.01); *A61N 1/0476* (2013.01);
(Continued)

(58) Field of Classification Search
CPC .. A61M 2205/507; G06F 3/014; A61B 5/486; A61B 5/6803; A61B 5/743; A61B 5/7445; A63F 2300/8082; A61N 5/0618
See application file for complete search history.

(56) References Cited

U.S. PATENT DOCUMENTS

| 9,265,965 B2 | 2/2016 | Fox et al. |
| 2010/0003656 A1* | 1/2010 | Kilgard ............. A61N 1/36014 434/262 |

(Continued)

FOREIGN PATENT DOCUMENTS

WO    00/74777 A1    12/2000

OTHER PUBLICATIONS

Mcfarland et al.; An EEG-Based Method for Graded Cursor Control; Phychology; 1993; pp. 77-81; 21; 1.

(Continued)

*Primary Examiner* — Christine H Matthews
(74) *Attorney, Agent, or Firm* — K&L Gates LLP (57) ABSTRACT

Systems, methods and techniques for providing sensory input to a subject through non-invasive brain stimulation are generally described. In some examples, an input signal related to an environment may be received. In various further examples, a communication to the subject may be determined in response to the input signal. In some examples, an output signal corresponding to the determined communication may be generated. Some further examples may comprise non-invasively stimulating a portion of the subject's brain with the output signal with a stimulation subsystem positioned outside of the subject's scalp. In various examples, the stimulation of the portion of the subject's brain may be effective in producing a sensory response perceivable by the subject.

19 Claims, 9 Drawing Sheets

(51) Int. Cl.
    *A61N 1/36*     (2006.01)
    *A61N 1/04*     (2006.01)
    *A61B 5/00*     (2006.01)
    *G06F 3/01*     (2006.01)

(52) U.S. Cl.
    CPC .......... *A61N 1/36025* (2013.01); *A61N 2/02* (2013.01); *G06F 3/015* (2013.01)

(56) References Cited

U.S. PATENT DOCUMENTS

| | | |
|---|---|---|
| 2010/0113863 A1 | 5/2010 | George et al. |
| 2013/0267759 A1 | 10/2013 | Jin |
| 2014/0316191 A1* | 10/2014 | de Zambotti .......... G06F 19/00 600/27 |

OTHER PUBLICATIONS

Menkes et al.; Right Frontal Lobe Slow Frequency Repetitive Transcranial Magnetic Stimulation (SF r-TMS) is an Effective Treatment for Depression: a Case-Control Pilot Study of Safety and Efficacy; *J. Neurol. Neurosurg. Psychiatry*; 1999; pp. 113-115; 67.

Pascual-Leone et al; Transcranial Magnetic Stimulation: Studying the Brain-Behaviour Relationship by Induction of 'Virtual Lesions'; *Philos. Trans. R. Society of London; B. Biol. Sci*;.1999; pp. 1229-1238; 354.

George et al; A Controlled Trial of Daily Left Prefrontal Cortex TMS for Treating Depression; Society of *Biological Psychiatry*; 2000; pp. 962-970; 48.

Cowey et al,;Magnetically Induced Phosphenes in Sighted, Blind and Blindsighted Observers; *NeuroReport*; 2000; pp. 3269-3273; II; Lippincott Wiliams & Wilkins; Oxford, UK.

Walsh et al.; Transcranial Magnetic Stimulation and Cognitive Neuroscience; *Nature Reviews, Neuroscience*; 2000; pp. 73-79; 1; McMillian Magazines Ltd.

Sing eat al; ROCR: Visualizing Classifier Performance in R; *Bioinformatics*; 2005; pp. 3940-3941; 21; 20; Oxford University Press.

Fawcett; An Introduction to ROC Analysis; *Pattern Recognition Letters*; 2005; pp. 861-874; 27; www.sciencedirect.com.

Devlin; Stimulating Language: Insights from TMS; *Brain*; 2006; pp. 610-622; 130; Department of Clinical Neurology, University of Oxford; Oxford, UK.

Cover et al.; Elements of Information Theory; 1991; John Wiley & Sons, Inc.

Silvanto et al.; Making the Blindsighted See. *Neuropsychologia*; 2007; pp. 3346-3350; 45; www.elsevier,com; Oxford, UK.

Bell et al.; Control of a Humanoid Robot by a Noninvasive Brain-Computer Interface in Humans; Journal of Neural Engineering; 2008; pp. 214-220; 5; Dept of Computer Science and Engineering, University of WA; Seattle, WA.

Meyer et al.; Package 'infotheo' Information—Theoretic Measures; 2015; http://homepage.meyerp.com/software.

Taylor et al.; The Neural Signature of Phosphene Perception; Hum. Brain Mapp; 2010; pp. 1408-1417; 31; School of Psychology, Birkbeck College, London, UK.

Thomson et al.; Perceiving Invisible Light Through a Somatosensory Cortical Prosthesis; *Nature Communications*; 2013; 4; 1482; Macmillan Publishers Ltd.

Lafleur et al.; Quadcopter Control in Three-Dimensional Space Using a Noninvasive Motor Imagery-Based Brain-Computer Interface; *Journal of Neural Engineering*; 2013; 4; 046003; University of Minnesota; Minneapolis, MN.

Cushman et al.; Multisensory Control of Multimodal Behavior: Do the Legs Know What the Tongue is Doing? *PLOS One*; 2013; 8; 11; e80465; www.plosone.org.

Grau et al.; Conscious Brain-to-Brain Communication in Humans Using Non-Invasive Technologies. PLOS One; 2014; 9; 8; e105225; www.plosone.org.

Rao et al; A Direct Brain-to-Brain Interface in Humans; 2014; 9; 11; e111332; www.plosone.org.

Aghajan et al.; Impaired Spatial Selectivity and Intact Phase Precession in Two-Dimensional Virtual Reality; *Nature Neuroscience*; 2014; pp. 121-128; 18; 1.

Terhune et al.; Phosphene Perception Relates to Visual Cortex Glutamate Levels and Covaries with Atypical Visuospatial Awareness; *Cerebral Cortex*; 2015; pp. 4341-4350; doi:10.1093/cercor/bhv015.

Stocco et al.; Playing 20 Questions with the Mind: Collaborative Problem Solving by Humans using a Brain-to-Brain Interface; 2015; DOI:10.1371/journal.pone.0137303; *PLOS One*.

Author unknown; Transcranial Magnetic Stimulation; Wikipedia; retrieved Sep. 13, 2016 from https://en.wikipedia.org/wiki/Transcranial_magnetic_stimulation?oldid=738015524.

Author unknown; Phosphene; Wikipedia; retrieved Sep. 13, 2016 from https://en.wikipedia.org/wiki/Phosphene?oldid=734207698.

\* cited by examiner

SENSORY INPUT THROUGH NON-INVASIVE BRAIN STIMULATION

CROSS-REFERENCE TO RELATED APPLICATIONS

This application claims the benefit of U.S. Provisional Application No. 62/244,582, filed Oct. 21, 2015, the disclosure of which is incorporated herein by reference in its entirety.

FIELD

This application relates to neurobiology and neurostimulation.

BACKGROUND

Brain-computer interfaces (BCIs) have been developed which allow electrical activity within the brain to be detected and interpreted by a computer. Such BCIs may allow brain signals to control a wide variety of devices, such as cursors, robots, and communication devices BCIs are often directed to mapping, augmenting, and/or repairing human cognitive or sensory-motor functions. In some examples, BCIs may be used to allow persons with disabilities to better interact with their environments. For example, BCIs have been used to attempt to restore damaged hearing, sight, and movement. BCIs have also been used to decode brain activity in rhesus monkeys, allowing the monkeys to control a robotic arm through the BCI. Various techniques, such as electroencephalography (EEG) may be used to detect electrical activity in the brain. Such electrical activity may be encoded into a signal by a computer. The signal may be transmitted using traditional network technologies and may be used to control various devices or decoded by a recipient computer to provide information about the neural activity of the monitored subject.

SUMMARY

Systems and methods are provided to produce sensory input through non-invasive stimulation of a subject's brain.

In accordance with embodiments of the present invention, a non-invasive method to stimulate a subject's brain may comprise receiving an input signal. In some examples, the method may further comprise determining, in response to the input signal, a communication to the subject. In another example, the method may further include generating an output signal corresponding to the determined communication. In still other examples, the method may further include non-invasively stimulating a portion of the subject's brain with the output signal with a stimulation subsystem positioned outside of the subject's scalp to produce a sensory response perceivable by the subject.

In some further example embodiments, the received input signal may correspond to information relating to a virtual reality environment or an augmented reality environment.

In various other example embodiments, the input signal may correspond to information relating to an environment, and the sensory response may provide a signal for interacting with the environment.

In various other examples, non-invasively stimulating the portion of the subject's brain with the output signal may comprise transcranial magnetic stimulation of the portion of the subject's brain.

In yet other example embodiments, non-invasively stimulating the portion of the subject's brain with the output signal may comprise transcranial current stimulation of the portion of the subject's brain.

In various other example embodiments, non-invasively stimulating the portion of the subject's brain with the output signal may comprise non-invasively stimulating the visual cortex of the subject's brain, and the sensory response perceivable by the subject may comprise a phosphene.

In still other example embodiments, non-invasively stimulating the portion of the subject's brain with the output signal may comprise non-invasively stimulating the somatic sensory cortex of the subject's brain, and the sensory response perceivable by the subject may comprise a touch sensation.

In another example embodiment, non-invasively stimulating the portion of the subject's brain with the output signal may comprise non-invasively stimulating the auditory cortex of the subject's brain, and the sensory response perceivable by the subject may comprise an auditory sensation.

In various further examples, the non-invasive method to stimulate a subject's brain may further comprise performing a calibration process. In some examples, the calibration process may include stimulating the portion of the subject's brain with a first magnitude stimulation signal, monitoring the subject's brain to determine that a state of the brain indicates that the first magnitude stimulation did not produce a perceivable sensory response, and stimulating the portion of the subject's brain at progressively increasing stimulation signal magnitudes until a second state of the brain indicates that a perceivable sensory response is produced.

In accordance with embodiments of the present invention, a computer-brain interface is generally described. In various examples, the computer-brain interface may include at least one processor, a non-invasive brain stimulation device, and a non-transitory memory. The non-transitory memory may store computer-executable instructions which when executed cause the at least one processor to perform a method comprising receiving an input signal. In further examples, the computer-executable instructions may cause the at least one processor to determine, in response to the input signal, a communication to a subject. In further examples, the computer-executable instructions may cause the at least one processor to generate an output signal corresponding to the determined communication. In some other examples, the computer-executable instructions may cause the at least one processor to non-invasively stimulate a portion of the subject's brain with the output signal with a stimulation subsystem positioned outside of the subject's scalp to produce a sensory response perceivable by the subject.

Still other embodiments of the present invention will become readily apparent to those skilled in the art from the following detailed description, which describes embodiments illustrating various examples of the invention. As will be realized, the invention is capable of other and different embodiments and its several details are capable of modifications in various respects, all without departing from the spirit and the scope of the present invention. Accordingly, the drawings and detailed description are to be regarded as illustrative in nature and not as restrictive.

DETAILED DESCRIPTION

In the following description, reference is made to the accompanying drawings that illustrate several embodiments of the present disclosure. It is to be understood that other embodiments may be utilized and system or process changes may be made without departing from the spirit and scope of the present disclosure. The following detailed description is not to be taken in a limiting sense, and the scope of the embodiments of the present invention is defined only by the claims of the issued patent. It is to be understood that drawings are not necessarily drawn to scale.

Various embodiments of the present disclosure provide improved systems and methods for providing sensory input through non-invasive brain stimulation. These embodiments may provide subjects with information about various environments and other external conditions which may be otherwise unavailable to the subject, for a variety of reasons, as described in further detail below. Additionally, various technical challenges presented when providing otherwise unperceivable information to a subject may be overcome using the techniques and systems described herein.

Figure 1:
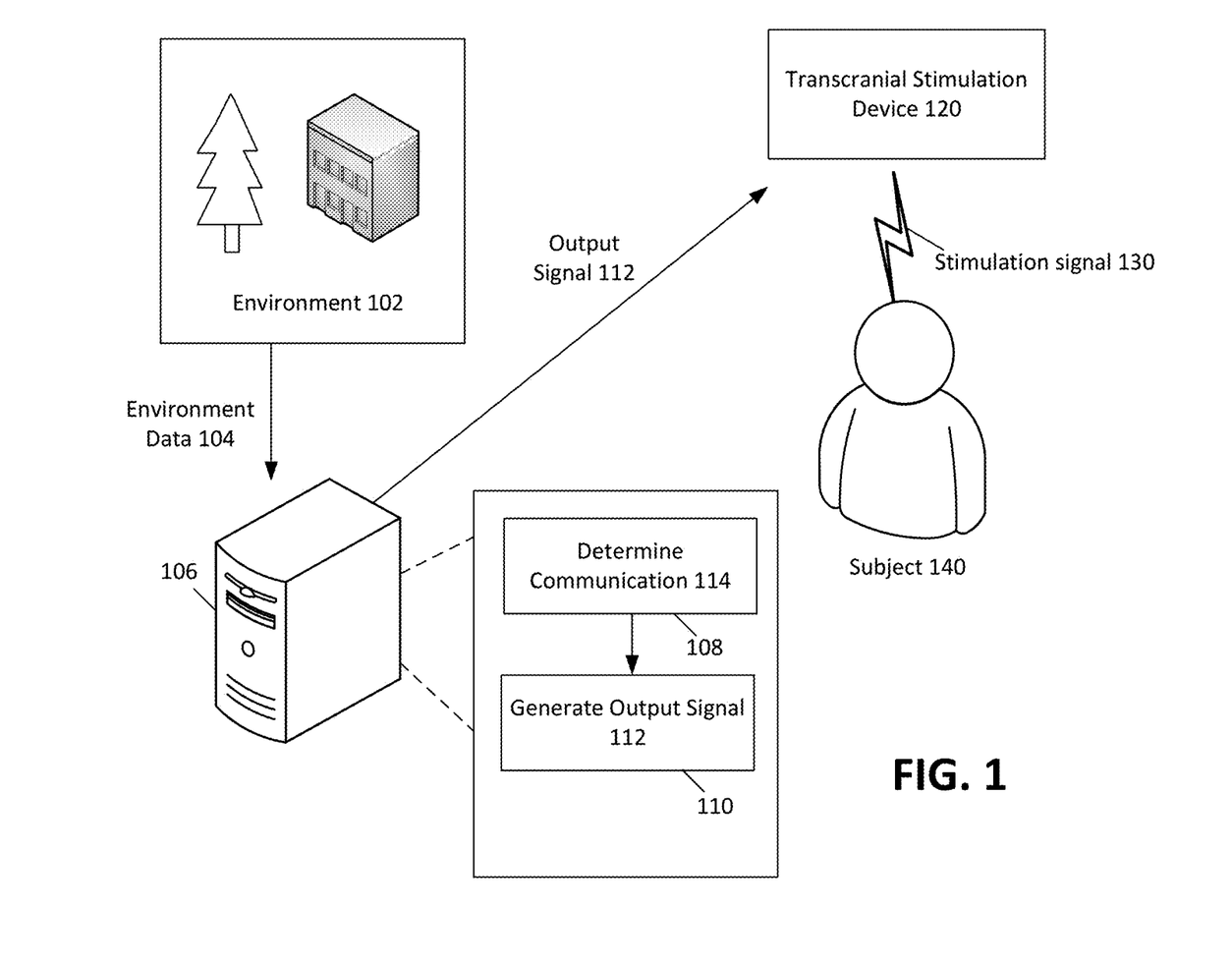
FIG. 1 depicts a system effective to induce a sensory response in a subject through non-invasive, transcranial brain stimulation, in accordance with various embodiments of the present disclosure.

FIG. 1 depicts a system effective to provide sensory input through non-invasive, transcranial brain stimulation, in accordance with various embodiments of the present disclosure. In various examples, a system for providing sensory input through non-invasive transcranial brain stimulation may include an environment 102, one or more computing devices 106, and a transcranial stimulation device 120. In various examples, the system depicted in FIG. 1 may be generally referred to as a computer-to-brain interface (CBI).

In some examples, environment 102 may be or may include a virtual environment, such as a computer-generated virtual reality (VR) environment and/or an electronic gaming environment with which a subject 140 is interacting through one or more computing devices (e.g., one or more of computing devices 106), a VR headset, one or more display screens, a gaming system, etc. In some further examples, environment 102 may include the actual physical environment in which a subject 140 is located. For example, environment 102 may be a room in which the subject 140 is located or an outdoor area in which the subject 140 is located. In various other examples, environment 102 may be a remote physical environment that the user is currently unable to perceive. For example, environment 102 may be a location distant from subject 140.

In some further examples, environment 102 may be an augmented reality environment mixing virtual computer-generated elements (such as computer-generated augmented reality skins overlaying real objects) with real elements, such as buildings, trees, people, and/or other physical objects.

One or more computing devices 106 (sometimes referred to herein as "computing device 106", for brevity) may be effective to gather and/or process data related to environment 102. For example, computing device 106 may be effective to determine environment data 104 related to environment 102. Environment data 104 may relate to visual information concerning the virtual reality environment, such as spatial information, text, data related to movement of objects, coordinate and/or other positional data, colors of objects, status information of objects, etc. In general, visual information may include any data that may be visually perceived by a user interacting with a virtual reality environment.

In various other examples, environment 102 may comprise a brain-computer-interface of another subject. In such examples, environment data 104 may include encoded signals detected from the brain of the other human subject and received by computing device 106.

Similarly, environment data 104 may relate to other features of environment 102, such as sounds, smells, tastes, or any other sensory information that may be perceivable and/or quantifiable by computing device 106. In some examples, computing device 106 may include several computing devices arranged to be in communication with one another through a network, such as a local area network or a wide area network such as the internet. In such examples, the various computing devices may form a cloud computing network effective to process environment data 104. For example, computing device 106 may gather and process environment data 104 to perform operation 108: determine a communication 114. As is described in further detail below, computing device 106 may include and/or may be configured to be in communication with one or more sensors for gathering environment data 104.

Communication 114 may comprise, for example, information to be conveyed to a subject 140 concerning environment 102. A few examples of such information may include sensory information, directions, instructions, and/or any other information regarding environment 102 and/or subject 140's interaction with environment 102. Communication 114 may be determined in accordance with instructions executed by computing device 106. Similarly, environment data 104 may be identified and/or collected based on instructions executed by computing device 106. In examples where environment 102 is a virtual reality environment or an augmented reality environment, computing device 106 may use one or more application programming interfaces to interact with environment 102 and collect environment data 104 from environment 102. In various other examples, computing device 106 may gather environment data 104 from environment 102 using one or more sensors. When environment 102 is a real, physical environment, a few examples of such sensors may include microphones, cameras, accelerometers, gyroscopes, positional sensors, thermometers, chemical and/or biological sensors, pressure sensors, etc. When environment 102 is a computer-generated environment, one or more computing devices, such as computing device 106 may determine environment data through communication with computing devices generating the computer-generated environment. For example, a computing device may use one or more application programming interfaces to monitor a virtual reality environment being executed by one or more virtual reality servers.

Upon determining a communication to be sent to a subject 140 at operation 108, computing device 106 may perform operation 110: generate an output signal 112. The output signal 112 may correspond to communication 114 determined at operation 108 and may comprise an encoding of communication 114. Output signal 112 may be provided to transcranial stimulation device 120. In various examples, transcranial stimulation device 120 may be referred to as a "stimulation subsystem" in the sense that one or more other components, such as computing device 106 may be involved in stimulation of the brain of subject 140. As will be described in further detail below, transcranial stimulation device 120 may receive output signal 112 and may generate a corresponding stimulation signal 130. Stimulation signal 130 may be provided in a non-invasive, transcranial manner to one or more portions of the brain of subject 140. Stimulation of the one or more portions of the brain of subject 140 with stimulation signal 130 may be effective to elicit one or more sensory responses in subject 140. For example, subject 140 may be able to perceive information relating to communication 114 through an induced artificial sensory response resulting from the stimulation of one or more portions of subject 140's brain with one or more stimulation signals 130. In various examples, a sensory response induced by stimulation signal 130 may provide the information in communication 114 regarding environment 102 to subject 140 and may allow subject 140 to better interact with the environment based on the elicited sensory response.

Some examples of transcranial stimulation devices 120 may include magnetic transcranial stimulation devices, electrical transcranial stimulation devices, ultrasound stimulation devices, etc. In various examples, different types of stimulation may be used when stimulating different portions of the brain in order to maximize the artificial sensory response induced in an individual. Additionally, as will be discussed in further detail below, varying magnitudes of stimulation signals 130 may be used as different individuals may show varying sensitivities to the particular stimulation signal 130 being used. Also, different individuals may exhibit different phenotypes that may reduce or enhance the effectiveness of stimulation signals 130. For example, varying skull thickness, brain size, and/or varying depth of various target sensory cortexes may affect the efficacy of sensory response elicited from a particular stimulation signal 130.

Transcranial magnetic stimulation may comprise one or more coils of electrically conductive material through which a current is passed in order to produce a magnetic flux. In one example, two coils are used in a "figure-eight" pattern. In such an example, the magnetic flux may be concentrated at the center of the figure-eight pattern, between the two coils. Accordingly, in some examples, the center of the figure-eight pattern may be placed close to the subject's scalp over the portion of the subject's brain that is to be stimulated in order to increase the magnitude of stimulation.

In transcranial electrical stimulation, electrical leads may be attached to the scalp of the subject. In some examples, the leads may be positioned such that alternating or direct current passes from a first lead positioned on the scalp, through the subject's head, through the target portion of the brain to be stimulated, to another lead on the scalp.

Although, in examples discussed below, visual sensory information is produced in a subject through non-invasive brain stimulation of the visual cortex, other sensory information may be produced through stimulation of portions of the brain corresponding to the particular sensation. For example, sensations of touch, audible sensations, olfactory sensations, taste sensations, and/or any other perceivable sensation controlled by a neurological response may be induced in a subject through appropriate stimulation of a portion or portions of the subject's brain that controls perception of the particular sensation or sensations to be induced in that subject.

Additionally, in some examples, different stimulation methods may be used for different portions of the brain. For example, while transcranial magnetic stimulation may be more effective for inducing phosphene production through magnetic stimulation of a subject's visual cortex, transcranial alternating current electrical stimulation may be more effective for stimulating the somatosensory cortex to elicit a sensation of touch in a subject. Similarly, ultrasound stimulation may be more effective in eliciting an olfactory sensation in a subject.

Figure 2:
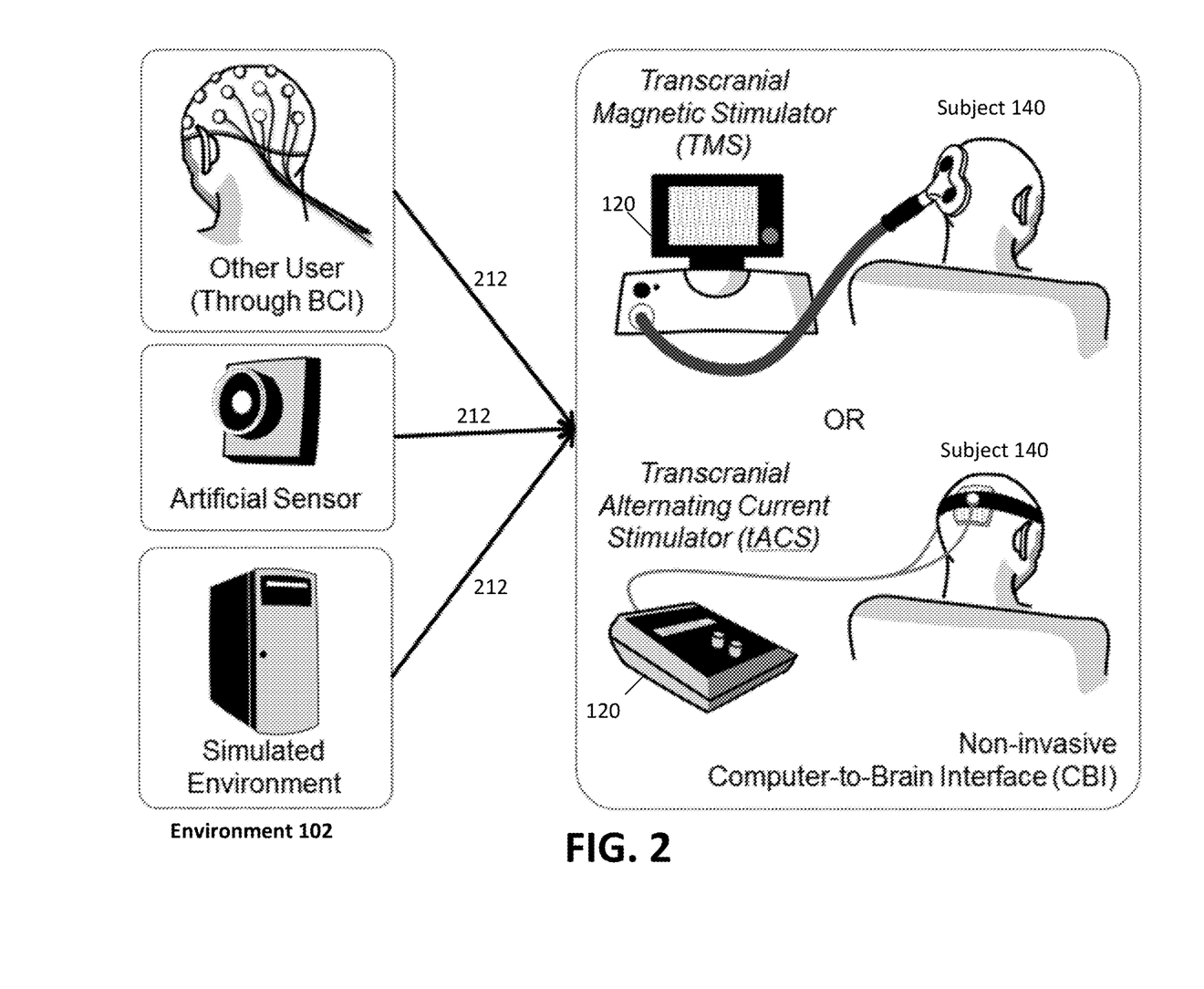
FIG. 2 depicts an example system effective to induce a sensory response in a subject from a variety of input sources using either transcranial magnetic stimulation or transcranial alternating current stimulation, in accordance with various embodiments of the present disclosure.

FIG. 2 depicts an example system effective to elicit a sensory response in a subject from a variety of input sources using either transcranial magnetic stimulation or transcranial alternating current stimulation, in accordance with various embodiments of the present disclosure.

FIG. 2 depicts three different example environments 102 that may be used to provide input to a non-invasive transcranial stimulation device—a brain-to-computer interface (BCI), one or more artificial sensors, and/or a simulated and/or virtual environment. As described above, environment data (e.g., environment data 104) may be determined from and/or provided by environment 102. The environment data may be processed by one or more computing devices (e.g., computing device 106 of FIG. 1) to determine a communication to be provided to the subject. The communication may be encoded into an output signal 212 and sent to a transcranial stimulation device.

FIG. 2 depicts two example non-invasive transcranial stimulation devices, a transcranial magnetic stimulator (TMS) and a transcranial alternating current stimulator (tACS). Output signal 212 may be received by the non-invasive transcranial stimulation device. The particular non-invasive transcranial stimulation device receiving output signal 212 may generate a stimulation signal corresponding to the output signal 212. As described above, a transcranial magnetic stimulator may generate a stimulation signal comprising a magnetic field that may be used to stimulate one or more portions of the brain of subject 140. Similarly, a transcranial alternating current stimulator may generate a stimulation signal comprising an electric current that may be used to stimulate one or more portions of the brain of subject 140. Stimulation of the one or more portions of subject 140's brain may elicit a sensory response in the subject 140.

Figure 3:
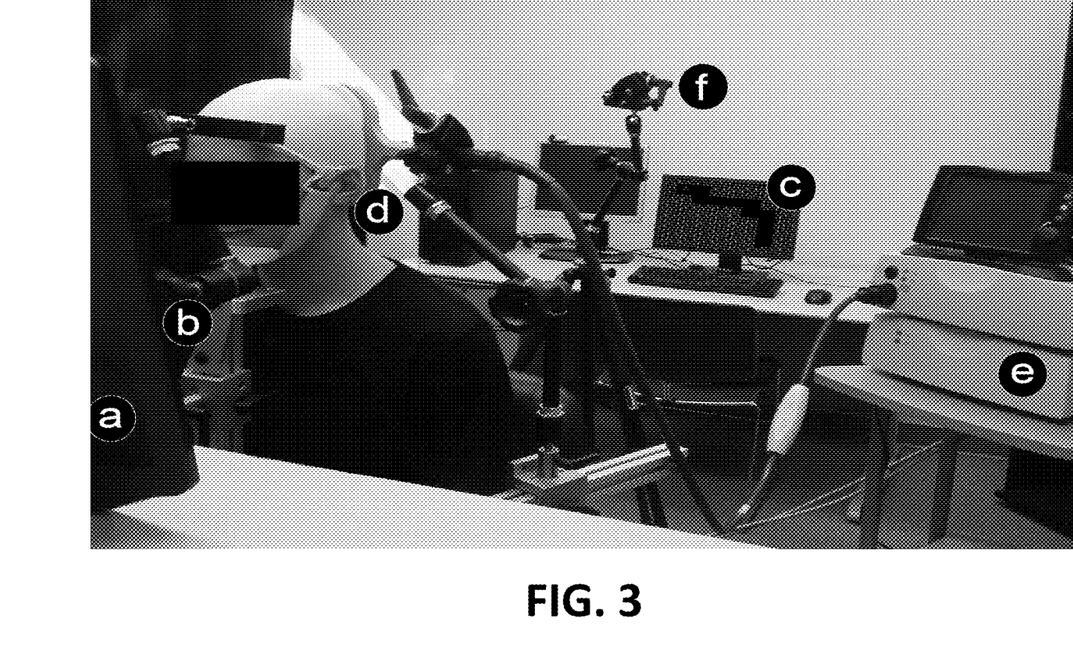
FIG. 3 depicts an example system effective to induce a sensory response in a subject interacting with a virtual reality environment, in accordance with various embodiments of the present disclosure.

FIG. 3 depicts an example system effective to induce a sensory response in a subject (e.g., subject 140 of FIG. 1) interacting with a virtual reality environment, in accordance with various embodiments of the present disclosure. FIGS. 2-6 describe an example experiment demonstrating an implementation of a system effective to provide sensory input through non-invasive, transcranial brain stimulation, in accordance with the general system described with reference to FIG. 1. The example system depicted in FIG. 3 comprises element (a) a touch screen monitor which the subject may use, in the current example, to interact with the virtual reality environment. The example system depicted in FIG. 3 further comprises a stabilizing unit (b) including a two-pronged head-and-chin rest used to immobilize the subject's head while interacting with the system depicted in FIG. 3. Monitor (c) depicts a visual representation of a two-dimensional virtual reality environment with which the subject is interacting. Monitor (c) is not visible to the subject. Element (d) is a transcranial magnetic stimulation device configured in a figure-eight shaped coil and situated over a portion of the patient's scalp corresponding to the visual cortex in the subject's brain. Element (d) is depicted as being powered by element (e), a magnetic stimulation signal generator. The coil of element (d) is depicted as being positioned over the subject's scalp using a laser pointer (f).

Figure 4:
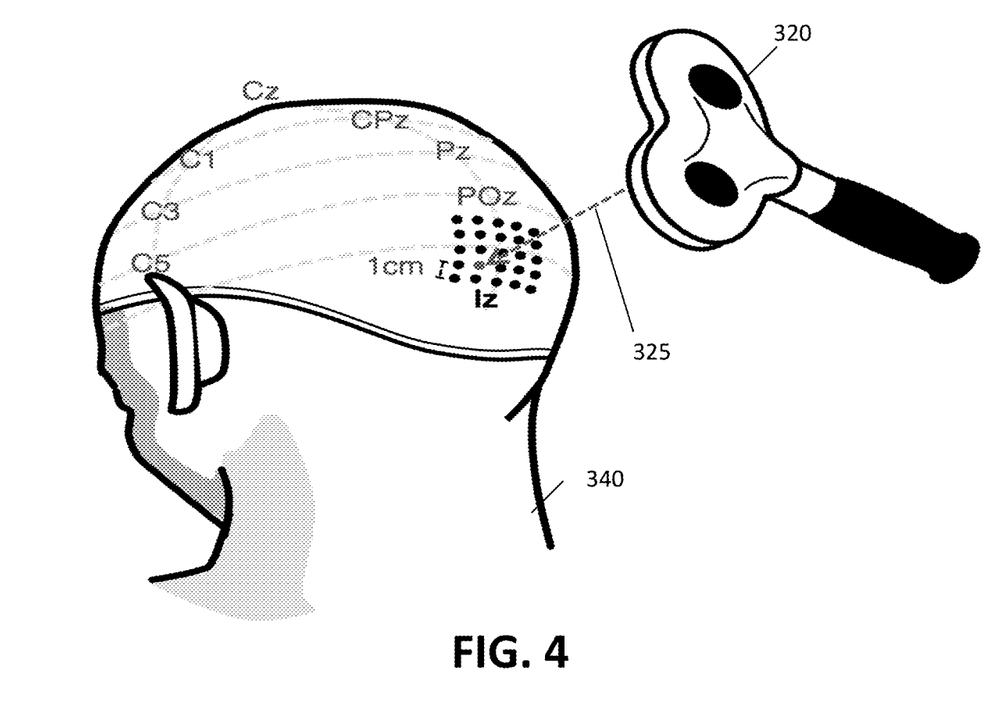
FIG. 4 depicts an example figure-eight shaped coil of the transcranial magnetic stimulation device, in accordance with various embodiments of the present disclosure.

FIG. 4 depicts an example figure-eight shaped coil of the transcranial magnetic stimulation device 320 (e.g., element (d) of FIG. 3). As will be described in further detail below, in various examples, portions of the subject 340's scalp (or head covering worn by the subject 340) may be marked in order to correctly position transcranial magnetic stimulation device 320 with respect to a target portion of the subject's brain to be stimulated. Additionally, a visible laser 325 may be used to position and/or center the transcranial magnetic stimulation device.

Returning to FIG. 3, the system depicted is one illustrative example implementation of the general computer-to-brain interface system described above with respect to FIG. 1. The subject in FIG. 3 is positioned so that monitor (c), depicting a two-dimensional virtual reality environment, is not within the subject's field of view. Elements (d) and (e) (the transcranial magnetic stimulation device configured in a figure-eight shaped coil and the magnetic stimulation signal generator, respectively) may be used to stimulate the visual cortex of the subject's brain and thereby elicit phosphenes, which are visually detected images that are not induced by light, but instead are induced by stimulation. In this illustrated example, temporary visual precepts of lines or spots that can occur upon neuromodulation of the visual cortex. As will be described in further detail below, the stimulation signal produced by elements (d) and (e) encode information about the two-dimensional virtual reality environment with which the subject is interacting (e.g., the two-dimensional virtual reality environment depicted on monitor (c)).

Figure 5:
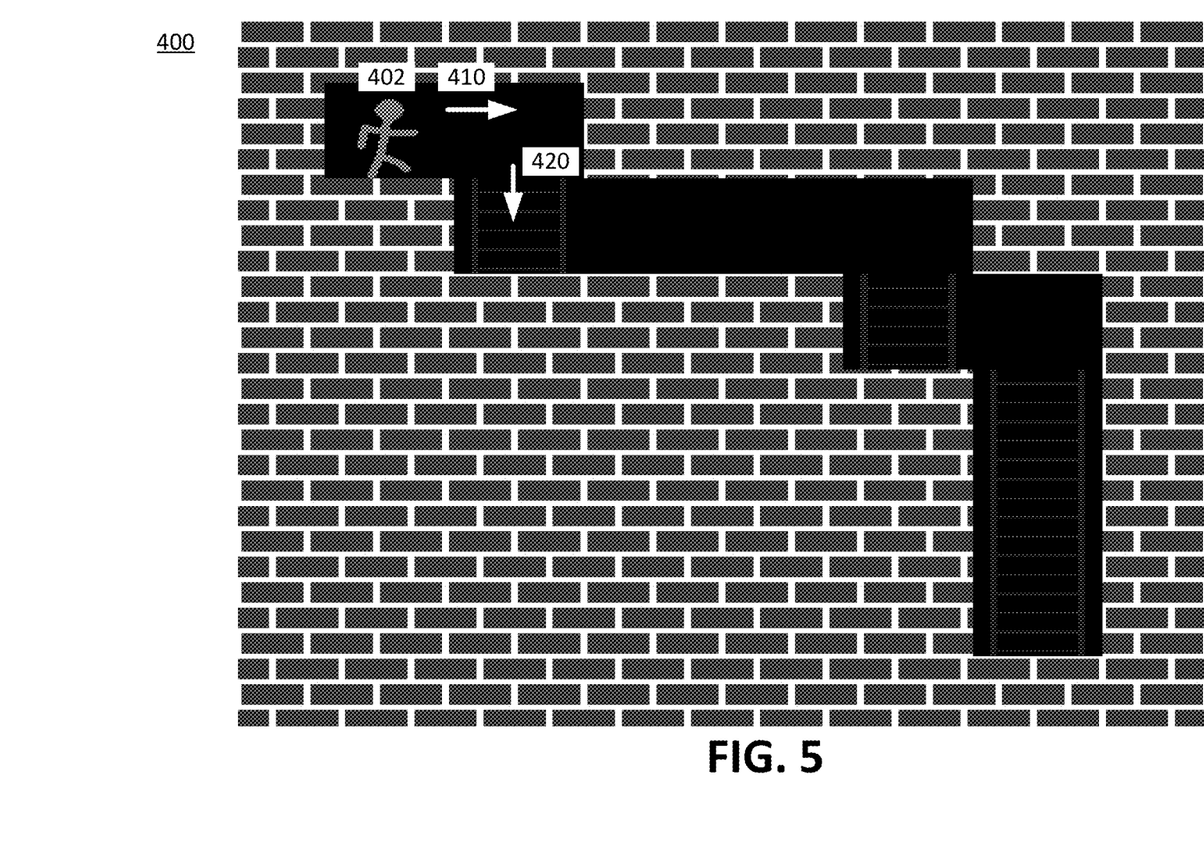
FIG. 5 depicts an example of a virtual reality environment that may be used to provide inputs to the systems depicted in FIGS. 1-4, in accordance with various example embodiments of the present disclosure.
Figure 6:
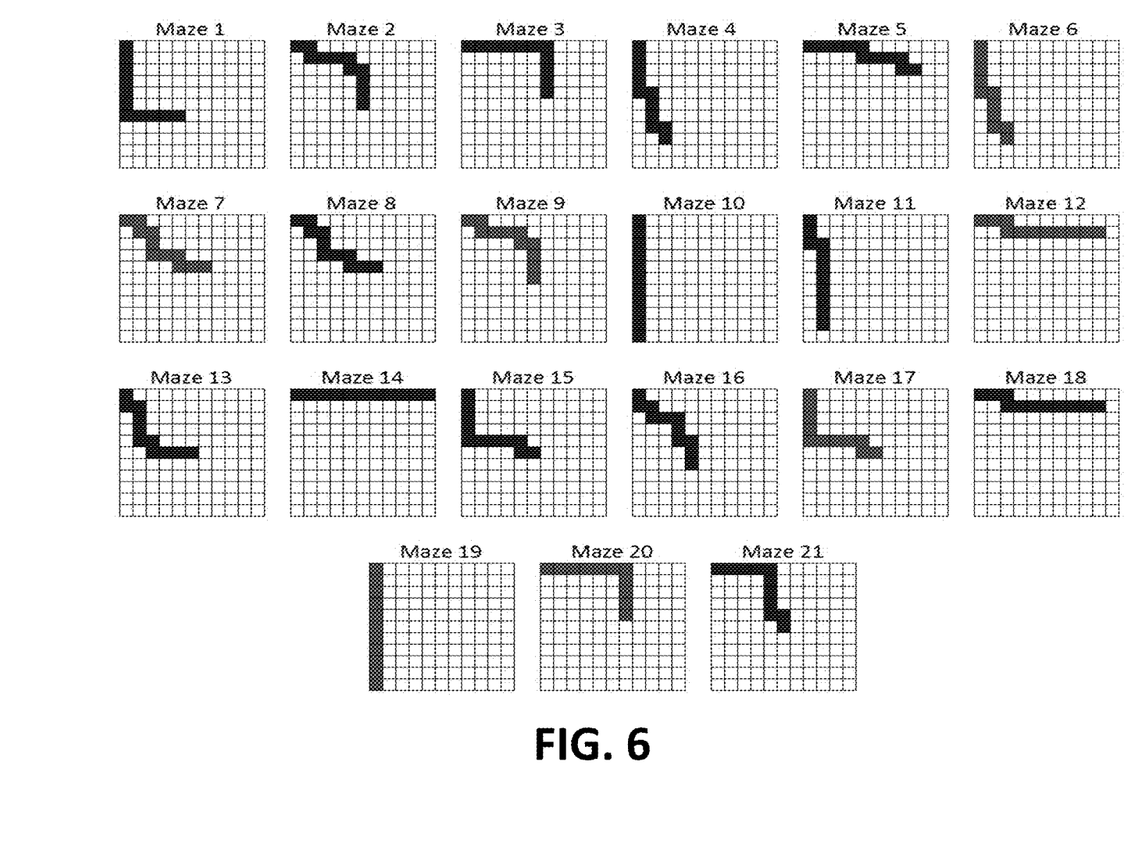
FIG. 6 depicts examples of experimental mazes and control mazes used in an experimental method of providing sensory input through non-invasive brain stimulation, in accordance with the present disclosure.

FIG. 5 depicts an example of a two-dimensional virtual reality environment 400 with which the subject depicted in FIG. 3 may interact. The subject interacting with two-dimensional virtual reality environment 400 may have an avatar 402 in the virtual reality environment. Various environment data, similar to environment data 104 described in FIG. 1, may be determined by one or more computing devices configured in communication with two-dimensional virtual reality environment 400. In one example, a computing device executing two-dimensional virtual reality environment 400 may determine environment data. In another example, one or more remote computing devices may provide two-dimensional virtual reality environment 400 and an application programming interface may be used to identify environment data related to two-dimensional virtual reality environment 400.

In the example depicted in FIG. 5, environment data may comprise a position of avatar 402 in two-dimensional virtual reality environment 400 and a distance of avatar 402 from a wall along forward direction 410. In some further examples, environment data may comprise information about the presence or absence of a downward path along downward direction 420 beneath avatar 402. It is to be appreciated that the two-dimensional virtual reality environment 400 and the environment data determined from two-dimensional virtual reality environment 400 is for illustrative purposes only. As described above with reference to FIG. 1, the particular environment used as an input to the computer-brain-interface system and the data from the particular environment may take a wide variety of different forms in accordance with the present disclosure.

Phosphene elicitation may be produced in the subject via single-pulse transmagnetic stimulation over the subject's primary visual cortex for augmenting human sensory capability. Information is relayed to the subject about obstacle depth in two-dimensional virtual reality environment 400 where the subject is deprived of visual information about two-dimensional virtual reality environment 400 in which the avatar 402 of the subject is navigating. The intensity of stimulation depends on the relative position of an avatar to the wall of the maze, such that being close to the wall along forward direction 410 causes the subject to perceive a phosphene and being far from a wall along forward direction 410 results in the absence of a phosphene. The subject's avatar 402 may advance in the maze if the subject correctly interprets the transcranial magnetic stimulation.

An example experimental method used for subjects to navigate two-dimensional virtual reality mazes (such as two dimensional virtual reality environment 400) through transcranial magnetic stimulation, is described below.

Generation of Mazes.

Fourteen experimental mazes and seven control mazes (see "Control Conditions" below) were generated and utilized for all participants. Mazes 1-5, 8, 10, 11, 13-16, 18, and 21 depicted in FIG. 6 comprise the fourteen experimental mazes used, and mazes 6, 7, 9, 12, 17, 19, and 20 comprise the seven control mazes used. All mazes were ten steps in length and consisted of a path that required a combination of forward or downward movements. The fourteen experimental mazes comprised of two sets of seven mazes. Each set of seven mazes consisted of one maze with each of zero through six "turns" randomly distributed throughout the maze, where a turn is a switch between forward and downward movements. The second set of seven experimental mazes represented the mirror image of the first set, such that all forward movements were replaced with downward movements and vice versa. The control mazes were selected such that for each of the one through six turn conditions, a maze from the original set or the mirrored set was randomly selected and added to the control set. The control maze with zero turns was selected to include only downward movements to avoid the trivial case in which a subject would likely finish the maze under the control conditions. The order in which the mazes were presented to the subject was randomized once, and kept consistent between subjects.

Control Conditions.

Figure 7:
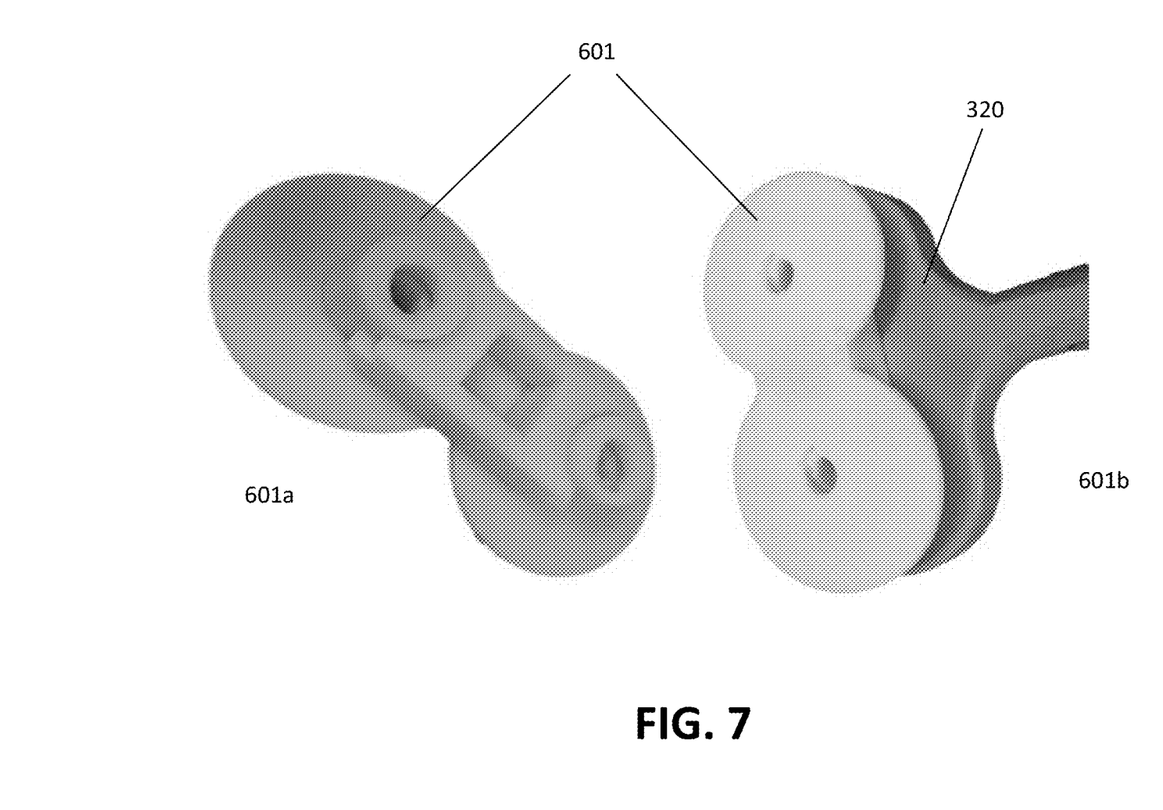
FIG. 7 depicts a plastic prop used as a control condition in an experimental method of providing sensory input through non-invasive brain stimulation, in accordance with the present disclosure.

In order to ensure that information came solely from the computer-brain interface, seven control mazes (e.g., mazes 6, 7, 9, 12, 17, 19, and 20 depicted in FIG. 6) were randomly intermixed with the 14 experimental games. During these trials, a custom-made plastic prop, whose design was intended to mimic the shape and texture of the coil of the transcranial magnetic stimulation device 320 was placed over the coil, separating the coil from the scalp of the subject by 20 mm. The plastic prop 601 is depicted in FIG. 7, and is shown prior to attachment (e.g., 601a) and as-attached to transcranial magnetic stimulation device 320 (e.g., 601b). This additional distance prevents the appearance of phosphenes due to transcranial magnetic stimulation while mimicking other sensory cues that could provide information about the subject's location in the maze, such as the noise and the vibration generated by the transcranial magnetic stimulation machine upon firing. This prop was tested for each subject during the thresholding phase (described below) to ensure its effectiveness in preventing phosphene perception.

Prior to the experiment, subjects were made aware of the existence of the control condition, but were not informed about which games the control condition would apply to or the ratio of experimental to control games. During the control condition, the TMS machine still fired at intensities appropriate to the avatar's location within the maze, irrelevant of its designation as a control game. Upon completion of the control maze, the subject was notified of the game's designation as part of the control set so as to not mislead the subject about their performance, which may impede their confidence in phosphene perception and influence their future performance.

The methodology with which the mazes were constructed ensured that one maze consisted of a straight hallway with no turns, which would cause all transcranial magnetic stimulation pulses to be subthreshold, and would thus mimic the perception of a control condition while not actually being a control maze. This was done to help prevent subjects from trying to guess whether the control condition was in place from a prolonged lack of phosphenes.

Determination of Phosphene Thresholds.

Prior to the experiment, each subject underwent a screening/calibration session in order to determine the intensity and location at which they reliably perceived phosphenes from a single pulse of transcranial magnetic stimulation. As convention, the intensity of stimulation is expressed as a percentage of the maximum output, which, in this case, is a 2.2 T magnetic field from a 70-mm figure-of-8 coil (Double 70 mm Alpha coil, Magstim, UK; FIG. 4) generated by a 660 V electric field from a biphasic transcranial magnetic stimulator such as element (e), shown in FIG. 3. The subject wore a tight-fitting cap, in which the location of the subject's inion was marked as a reference point for the stimulation process. A 4×4 cm grid of locations arranged in one-centimeter spaced rows and columns was then drawn one centimeter dorsal to the subject's inion (FIG. 3). For a given location, the suitability as a candidate "hotspot" for stimulation was determined by administering seven pulses of increasing magnitude, in increments of 5%, starting at 45%. Each subject's brain was monitored to determine if a state of the subject's brain indicated that a phosphene was produced. If the subject did not perceive a phosphene by the 75% mark, a new location was examined. Based on the results of Stocco et al. 2015, the first stimulation site examined was 2 cm dorsal, 1 cm left of the inion. Subsequent sites were then examined at increasing distance from this starting point. The first location at which the subject could perceive phosphenes at intensities less than 75% was designated as the target site for the stimulation hotspot. For safety, the subject was not stimulated more than once in a given eight second interval, either during the thresholding procedure or during the experimental session. The above-threshold intensity was determined as the lowest intensity for which the subject reported phosphene perception for ten consecutive stimulations. Conversely, the subthreshold intensity was determined as the largest intensity for which no phosphene was perceived for 10 consecutive stimulations. The control condition was then tested to ensure that participants could not perceive phosphenes when stimulated at the above-threshold intensity.

It should be noted that this method of phosphene perception implicitly accounts for minute individual differences between subjects, such varying skull thickness or neural architecture. Additionally, only a subset of all possible stimulation locations and parameters are examined. While a more reliable stimulation site may exist, the first reliable location was selected in order to minimize the number of stimulations administered during the thresholding phase. Therefore, because the choice of the location was not optimized for each subject, results may have been an underestimate the participants' achievable performance.

Experimental Paradigm

The subject sat in a darkened room in front of a touchscreen computer monitor (e.g., monitor (a) depicted in FIG. 3) that displayed a fixation cross. A pair of 36 dB noise-cancelling earplugs were used to help mask potential external cues and allow for better concentration. The transcranial magnetic stimulation coil was placed over the subject's occipital lobe at a location determined during the thresholding procedure (described above). Now with reference to FIG. 5, the subject's avatar 402 started in the upper left portion of the maze. Environment data was collected from the two-dimensional virtual reality environment 400. For example, if avatar 402 was directly in front of a wall along forward direction 410, such information was relayed to a computing device, such as computing device 106 of FIG. 1. The computing device determines a communication to provide to the subject based on the environment data. In the example experiment, the computing device may determine that the communication to be transmitted to the subject relates to avatar 402's position with respect to an obstacle (e.g., a wall) along forward direction 410. The computing device may encode the communication into an output signal. In the current example experiment, the computing device may encode the communication concerning avatar's position with respect to a wall in two-dimensional virtual reality environment 400 into a transcranial magnetic stimulation pulse. The output signal may be sent to the transcranial magnetic stimulation device. In the current example, the transcranial magnetic stimulation pulse signal may be sent to the transcranial magnetic stimulation device 320 (FIG. 3) which may, in turn, stimulate the subject's visual cortex using the transcranial magnetic stimulation pulse corresponding to the output signal.

In the example experiment, if avatar 402 was directly in front of a wall along forward direction 410, an above-threshold transcranial magnetic stimulation pulse was fired; otherwise, a subthreshold pulse was fired—indicating that a downward path was available for avatar 402. Note that the maze may be displayed on a second screen on monitor (c) (FIG. 3) visible only to the experimenter, and remained hidden from the subjects until the end of each maze. Instead, the screen visible to participants displayed a fixation sign cross while they waited for the next stimulation. Two seconds after the transcranial magnetic stimulation pulse fired, a question box appeared asking if the subject wishes to move forward in the maze or down a ladder. To avoid potential confusion, a reminder that the presence of a phosphene corresponds to a downward movement also displayed on screen. The subject answered the question by hitting one of two buttons on the touchscreen computer monitor to move forward or downward. If the subject identified the necessary movement correctly, their avatar advanced one space in that direction. If the subject misinterpreted the stimulation, they did not advance forward in the maze; in this case, the avatar remained in the same location and the same intensity stimulation was fired in the next time step, effectively repeating the time step. Each maze required 10 correct steps to be traversed completely. Correspondingly, each subject was given 10 stimulations per maze, and thus 10 opportunities to move. After the 10 simulations, the maze was displayed on the subject's screen to allow them to view their avatar's final location within the maze, and the subject was notified if that game was part of the control set. The maze was then hidden from their view as the next game commenced. Prior to the start of each game, the experimenter examined the subject's head position and relative coil position using a guiding laser pointed at the stimulation site (FIG. 3). If the next maze was a part of the control set, the experimenter attached the control prop 601 (FIG. 7) to the transcranial magnetic stimulation coil when re-adjusting head position. To keep the timing of the operations consistent across different conditions, the experimenter mimicked the procedure of inserting the control prop before every trial, including experimental trials.

Results.

On average, participants completely traversed 70% of the mazes under the experimental conditions and 0% in the control conditions. The difference was statistically significant (paired t(4)=3.89, p<0.02; FIG. 7a). Note that, as participants needed ten consecutive correct categorizations in order to complete a maze, a single mistake caused them to fall short of traversing the entire maze. Therefore, this analysis is a conservative measure of performance. A more sensitive measure would be the number of correct steps performed by participants under each condition. Participants completed an average of 92% of the steps in the experimental condition, significantly more than 15.4% of the steps in the control condition. In the control conditions, an ideal observer would always assume that, since no phosphenes are being perceived, he or she should always move forward. This would result in correctly performing only the initial forward movements for the control mazes and getting "stuck" at the first wall obstacle. This represents 14.2% of the total number of movements and is thus the baseline performance for the control condition.

Among other potential benefits, systems and methods designed in accordance with the present disclosure may allow for subjects to interpret and interact with various environments which the subject may otherwise be unable to perceive. The environmental inputs can be real environmental inputs, such as sights and sounds from the physical world, or the environmental inputs may be computer-generated inputs such as data about a virtual reality environment. In some examples, a subject may be otherwise unable to perceive the virtual environment, but through stimulation of various portions of the subject's brain, the subject may receive artificial sensory information corresponding to the virtual environment. Additionally, systems and methods designed in accordance with the present disclosure may allow for subjects with sensory disabilities to better interact with their environment. For example, a sensory cortex of a deaf or blind person may be stimulated in order to provide the person with sensory input (e.g., auditory information, visual information) about the surrounding environment that the person may otherwise be unable to perceive. In the example of a blind person, the visual cortex may be stimulated to elicit visual information about the blind person's environment, though the portion of the brain stimulated need not correspond to an area of the brain related to the disability. For example, the blind person's motor cortex may be stimulated so that a touch sensation is received in the blind person's hand whenever the blind person is approaching a wall or obstacle in their path.

Figure 8:
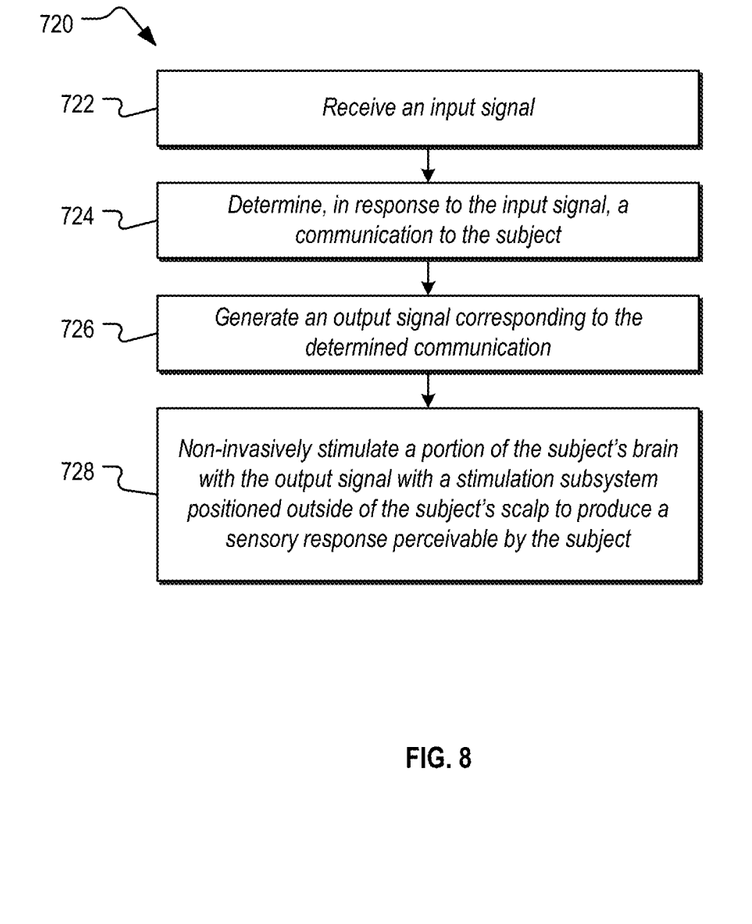
FIG. 8 depicts an example process that can be used to non-invasively stimulate a subject's brain, in accordance with various aspects of the present disclosure.

FIG. 8 depicts an example process that can be used to non-invasively stimulate a subject's brain, in accordance with various aspects of the present disclosure. The process of FIG. 8 may begin at operation 722: "Receive an input signal". In some examples, the input signal may be received by a computing device from an environment, such as environment 102 described in FIG. 1. The input signal may comprise environment data 104 related to the particular environment 102.

The process of FIG. 8 may continue from operation 722 to operation 724: "Determine, in response to the input signal, a communication to the subject." At operation 724, a computing device, such as computing device 106 depicted in FIG. 1, may determine a communication, such as communication 114 described above in reference to FIG. 1. The communication may comprise information to be conveyed to a subject regarding an environment with which the subject is interacting.

The process of FIG. 8 may continue from operation 724 to operation 726: "Generate an output signal corresponding to the determined communication." At operation 726, a computing device, such as computing device 106 of FIG. 1, may generate an output signal corresponding to the determined communication. In various examples, the communication may be encoded in the output signal. The output signal may be transmitted to a non-invasive stimulation subsystem, such as transcranial stimulation device 120 depicted in FIG. 1.

The process of FIG. 8 may continue from operation 726 to operation 728: "Non-invasively stimulate a portion of the subject's brain with the output signal with a stimulation subsystem positioned outside of the subject's scalp to produce a sensory response perceivable by the subject." At operation 728, the output signal from operation 726 may be used to generate a stimulation signal, such as stimulation signal 130 described above in reference to FIG. 1, that may be provided by a stimulation subsystem and used to non-invasively stimulate a portion of the subject's brain. The stimulation of the portion of the subject's brain may be effective to produce a sensory response perceivable by the subject. For example, the stimulation of the visual cortex of the patient's brain may induce a phosphene which the subject may see. In another example, stimulation of the subject's motor cortex may produce a touch sensation.

Figure 9:
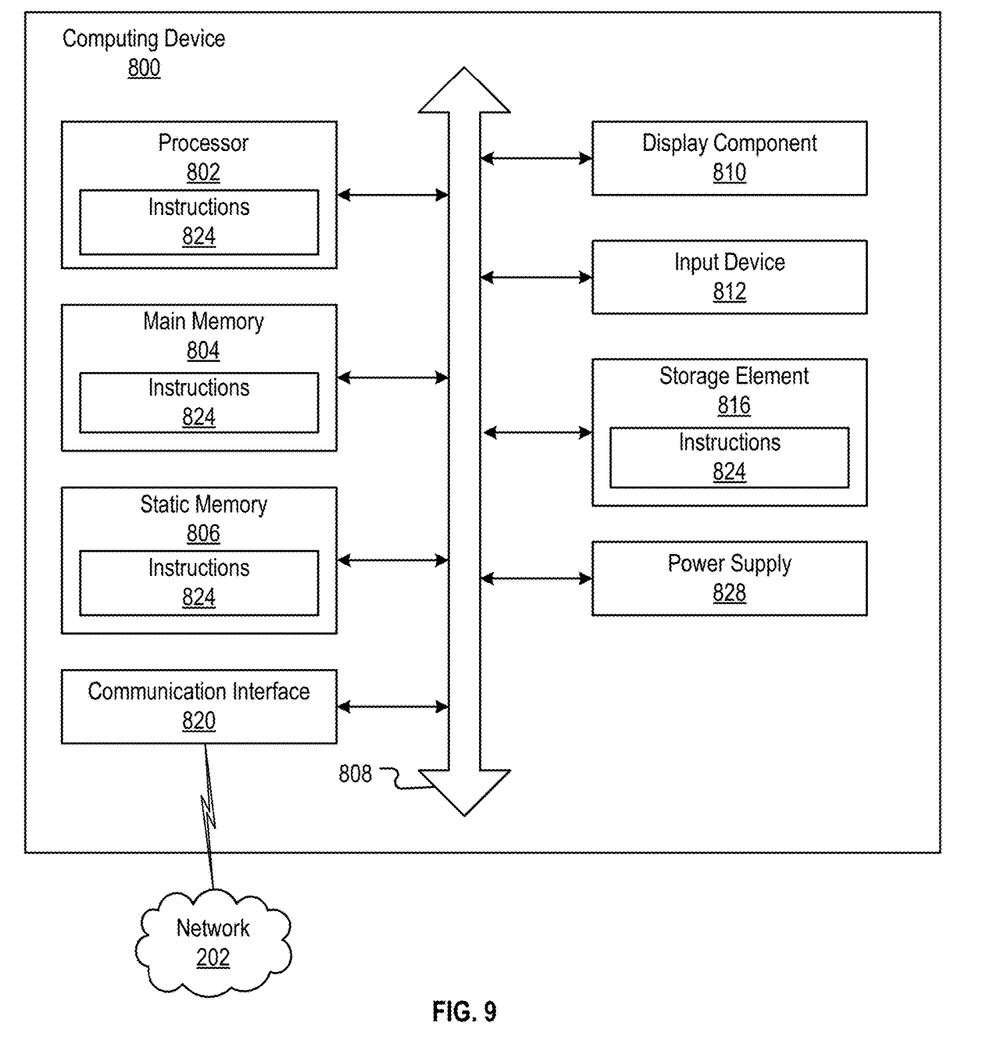
FIG. 9 depicts a computing device effective to produce signals for providing sensory input through non-invasive brain stimulation.

Referring to FIG. 9, the block diagram illustrates components of a computing device 800, according to some example embodiments, able to read instructions 824 from a non-transitory machine-readable storage medium (e.g., a hard drive storage system) and perform any one or more of the methodologies discussed herein, in whole or in part. Specifically, FIG. 9 shows the computing device 800 in the example form of a computer system within which the instructions 824 (e.g., software, a program, an application, an applet, an app, or other executable code) for causing the computing device 800 to perform any one or more of the methodologies discussed herein may be executed, in whole or in part. For example, the one or more computing devices 106 discussed above with reference to FIG. 1 may be implemented in a computing architecture similar to that of computing device 800.

In alternative embodiments, the computing device 800 operates as a standalone device or may be connected (e.g., networked) to other computing devices. In a networked deployment, the computing device 800 may operate in the capacity of a server computing device or a client computing device in a server-client network environment, or as a peer computing device in a distributed (e.g., peer-to-peer) network environment. The computing device 800 may include hardware, software, or combinations thereof, and may, as example, be a server computer, a client computer, a personal computer (PC), a tablet computer, a laptop computer, a netbook, a cellular telephone, a smartphone, a set-top box (STB), a personal digital assistant (PDA), a web appliance, a network router, a network switch, a network bridge, or any computing device capable of executing the instructions 824, sequentially or otherwise, that specify actions to be taken by that computing device. Further, while only a single computing device 800 is illustrated, the term "computing device" shall also be taken to include any collection of computing devices that individually or jointly execute the instructions 824 to perform all or part of any one or more of the methodologies discussed herein.

The computing device 800 includes a processor 802 (e.g., a central processing unit (CPU), a graphics processing unit (GPU), a digital signal processor (DSP), an application specific integrated circuit (ASIC), a radio-frequency integrated circuit (RFIC), or any suitable combination thereof), a main memory 804, and a static memory 806, which are configured to communicate with each other via a bus 808. The processor 802 may contain microcircuits that are configurable, temporarily or permanently, by some or all of the instructions 824 such that the processor 802 is configurable to perform any one or more of the methodologies described herein, in whole or in part. For example, a set of one or more microcircuits of the processor 802 may be configurable to execute one or more modules (e.g., software modules) described herein.

The computing device 800 may further include a display component 810. The display component 810 may comprise, for example, one or more devices such as cathode ray tubes (CRTs), liquid crystal display (LCD) screens, gas plasma-based flat panel displays, LCD projectors, or other types of display devices.

The computing device 800 may include one or more input devices 812 operable to receive inputs from a user. The input devices 812 can include, for example, a push button, touch pad, touch screen, wheel, joystick, keyboard, mouse, trackball, keypad, accelerometer, light gun, game controller, or any other such device or element whereby a user can provide inputs to the computing device 800. These input devices 812 may be physically incorporated into the computing device 800 or operably coupled to the computing device 800 via wired or wireless interface. For computing devices with touchscreen displays, the input devices 812 can include a touch sensor that operates in conjunction with the display component 810 to permit users to interact with the image displayed by the display component 806 using touch inputs (e.g., with a finger or stylus).

The computing device 811 may also include at least one communication interface 820, comprising one or more wireless components operable to communicate with one or more separate devices within a communication range of the particular wireless protocol. The wireless protocol can be any appropriate protocol used to enable devices to communicate wirelessly, such as Bluetooth, cellular, IEEE 802.11, or infrared communications protocols, such as an IrDA-compliant protocol. It should be understood that the communication interface 820 may also or alternatively comprise one or more wired communications interfaces for coupling and communicating with other devices.

The computing device 800 may also include a power supply 828, such as, for example, a rechargeable battery operable to be recharged through conventional plug-in approaches or through other approaches, such as capacitive charging. Alternatively, the power supply 828 may comprise a power supply unit which converts AC power from the power grid to regulated DC power for the internal components of the device 800.

The computing device 800 may also include a storage element 816. The storage element 816 includes the machine-readable medium on which are stored the instructions 824 embodying any one or more of the methodologies or functions described herein. The instructions 824 may also reside, completely or at least partially, within the main memory 804, within the processor 802 (e.g., within the processor's cache memory), or both, before or during execution thereof by the computing device 800. The instructions 824 may also reside in the static memory 806.

Accordingly, the main memory 804 and the processor 802 may also be considered machine-readable media (e.g., tangible and non-transitory machine-readable media). The instructions 824 may be transmitted or received over a network 202 via the communication interface 820. For example, the communication interface 820 may communicate the instructions 824 using any one or more transfer protocols (e.g., HTTP).

The computing device 800 may be implemented as any of a number of electronic devices, such as a tablet computing device, a smartphone, a media player, a portable gaming device, a portable digital assistant, a laptop computer, or a desktop computer. In some example embodiments, the computing device 800 may have one or more additional input components (e.g., sensors or gauges) (not shown). Examples of such input components include an image input component (e.g., one or more cameras), an audio input component (e.g., a microphone), a direction input component (e.g., a compass), a location input component (e.g., a GPS receiver), an orientation component (e.g., a gyroscope), a motion detection component (e.g., one or more accelerometers), an altitude detection component (e.g., an altimeter), and a gas detection component (e.g., a gas sensor). Inputs harvested by any one or more of these input components may be accessible and available for use by any of the modules described herein.

As used herein, the term "memory" refers to a non-transitory machine-readable medium capable of storing data temporarily or permanently and may be taken to include, but not be limited to, random-access memory (RAM), read-only memory (ROM), buffer memory, flash memory, and cache memory. The machine-readable medium is non-transitory in that it does not embody a propagating signal. While the machine-readable medium is described in example embodiments as a single medium, the term "machine-readable medium" should be taken to include a single medium or multiple media (e.g., a centralized or distributed database, or associated caches and servers) able to store instructions 824. The term "machine-readable medium" shall also be taken to include any medium, or combination of multiple media, that is capable of storing the instructions 824 for execution by the computing device 800, such that the instructions 824, when executed by one or more processors of the computing device 800 (e.g., processor 802), cause the computing device 800 to perform any one or more of the methodologies described herein, in whole or in part. Accordingly, a "machine-readable medium" refers to a single storage apparatus or device such as computing devices 110, 130, 140, or 150, as well as cloud-based storage systems or storage networks that include multiple storage apparatus or devices such as computing devices 110, 130, 140 or 150. The term "machine-readable medium" shall accordingly be taken to include, but not be limited to, one or more tangible (e.g., non-transitory) data repositories in the form of a solid-state memory, an optical medium, a magnetic medium, or any suitable combination thereof.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show details of the invention in more detail than is necessary for the fundamental understanding of the invention, the description taken with the drawings and/or examples making apparent to those skilled in the art how the several forms of the invention may be embodied in practice.

As used herein and unless otherwise indicated, the terms "a" and "an" are taken to mean "one," "at least one" or "one or more." Unless otherwise required by context, singular terms used herein shall include pluralities and plural terms shall include the singular.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While specific embodiments and examples for the disclosure are described herein for illustrative purposes, various equivalent modifications are possible within the scope of the disclosure, as those skilled in the relevant art will recognize. Such modifications may include, but are not limited to, changes in the dimensions and/or the materials shown in the disclosed embodiments.

Specific elements of any embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Therefore, it should be understood that the invention can be practiced with modification and alteration within the spirit and scope of the appended claims. The description is not intended to be exhaustive or to limit the invention to the precise form disclosed. It should be understood that the invention can be practiced with modification and alteration and that the invention be limited only by the claims and the equivalents thereof.

What is claimed is:

1. A method for interacting with a virtual environment, the method comprising:
receiving an input signal from the virtual environment;
determining, in response to the input signal, a communication about the virtual environment;
generating an output signal corresponding to the determined communication; and
non-invasively and transcranially stimulating a portion of a brain of a subject with the output signal with a stimulation subsystem positioned outside of a scalp of the subject to produce a sensory response perceivable by the subject, wherein the non-invasively and transcranially stimulating comprises transcranial ultrasound stimulation of the portion of the brain of the subject.

2. The method of claim 1, wherein:
the non-invasively and transcranially stimulating the portion of the brain of the subject comprises non-invasively stimulating a portion of the brain corresponding to perception of visual sensation; and
the sensory response comprises a phosphene.

3. The method of claim 1, wherein the sensory response provides information related to an orientation or position of an avatar of the subject in the virtual environment.

4. The method of claim 1, wherein:
the non-invasively and transcranially stimulating the portion of the brain of the subject comprises non-invasively stimulating a portion of the brain of the subject corresponding to perception of auditory sensation; and
the sensory response comprises an auditory sensation.

5. The method of claim 1, wherein:
the non-invasively and transcranially stimulating the portion of the brain of the subject comprises non-invasively stimulating a portion of the brain of the subject corresponding to somatosensory perception; and
the sensory response comprises a touch sensation.

6. The method of claim 1, wherein the non-invasively and transcranially stimulating comprises transcranial current stimulation of the portion of the brain of the subject.

7. The method of claim 1, wherein the non-invasively and transcranially stimulating comprises transcranial magnetic stimulation of the portion of the brain of the subject.

8. The method of claim 1, wherein:
the non-invasively and transcranially stimulating the portion of the brain of the subject comprises non-invasively stimulating a portion of the brain of the subject corresponding to perception of olfactory sensations; and
the sensory response comprises an olfactory sensation.

9. The method of claim 1, wherein:
the non-invasively and transcranially stimulating the portion of the brain of the subject comprises non-invasively stimulating a portion of the brain of the subject corresponding to perception of taste sensations; and
the sensory response comprises a taste sensation.

10. A method for interacting with a virtual environment, the method comprising:
receiving an input signal from the virtual environment;
determining, in response to the input signal, a communication about the virtual environment;
generating an output signal corresponding to the determined communication;
non-invasively and transcranially stimulating a portion of a brain of a subject with the output signal with a stimulation subsystem positioned outside of a scalp of the subject to produce a sensory response perceivable by the subject, wherein the non-invasively and transcranially stimulating comprises transcranial ultrasound stimulation of the portion of the brain of the subject; and receiving a command effective to perform an action in the virtual environment.

11. The method of claim 10, wherein the command is effective to cause an avatar of the subject in the virtual environment to perform the action.

12. The method of claim 10, wherein:
the non-invasively and transcranially stimulating the portion of the brain of the subject comprises non-invasively stimulating a portion of the brain corresponding to perception of visual sensation; and
the sensory response comprises a phosphene.

13. The method of claim 10, wherein the sensory response provides information related to an orientation or position of an avatar of the subject in the virtual environment.

14. The method of claim 10, wherein:
the non-invasively and transcranially stimulating the portion of the brain of the subject comprises non-invasively stimulating a portion of the brain of the subject corresponding to perception of auditory sensation; and
the sensory response comprises an auditory sensation.

15. The method of claim 10, wherein:
the non-invasively and transcranially stimulating the portion of the brain of the subject comprises non-invasively stimulating a portion of the brain of the subject corresponding to somatosensory perception; and
the sensory response comprises a touch sensation.

16. The method of claim 10, wherein the non-invasively and transcranially stimulating comprises transcranial current stimulation of the portion of the brain of the subject.

17. The method of claim 10, wherein the non-invasively and transcranially stimulating comprises transcranial magnetic stimulation of the portion of the brain of the subject.

18. The method of claim 10, wherein:
the non-invasively and transcranially stimulating the portion of the brain of the subject comprises non-invasively stimulating a portion of the brain of the subject corresponding to perception of olfactory sensations; and
the sensory response comprises an olfactory sensation.

19. The method of claim 10, wherein:
the non-invasively and transcranially stimulating the portion of the brain of the subject comprises non-invasively stimulating a portion of the brain of the subject corresponding to perception of taste sensations; and
the sensory response comprises a taste sensation.

* * * * *